(12) United States Patent
Hemblade

(10) Patent No.: US 7,878,047 B2
(45) Date of Patent: Feb. 1, 2011

(54) MONITORING PARTICLES IN A FLUID STREAM

(75) Inventor: Barry John Hemblade, Hove (GB)

(73) Assignee: Teledyne Cormon Limited, Lancing (GB)

( * ) Notice: Subject to any disclaimer, the term of this patent is extended or adjusted under 35 U.S.C. 154(b) by 461 days.

(21) Appl. No.: 12/092,252

(22) PCT Filed: Nov. 1, 2006

(86) PCT No.: PCT/GB2006/004073

§ 371 (c)(1),
(2), (4) Date: Apr. 30, 2008

(87) PCT Pub. No.: WO2007/052022

PCT Pub. Date: May 10, 2007

(65) Prior Publication Data

US 2008/0282781 A1    Nov. 20, 2008

(30) Foreign Application Priority Data

Nov. 1, 2005   (GB) ................................. 0522312.8
Apr. 28, 2006  (GB) ................................. 0608535.1

(51) Int. Cl.
*G01N 15/06* (2006.01)
(52) U.S. Cl. ...................................... 73/61.75
(58) Field of Classification Search .................. 73/61.75
See application file for complete search history.

(56) References Cited

U.S. PATENT DOCUMENTS 3,068,694 A   10/1958   Worswick
3,841,144 A   10/1974   Baldwin
4,315,428 A    2/1982   Stuivenwold et al.
4,674,337 A    6/1987   Jonas (Continued)

FOREIGN PATENT DOCUMENTS

EP          0 483 578           5/1992

(Continued)

OTHER PUBLICATIONS

EPIPO; Examination Report in related foreign application (GB 0608535.1) which is one of the foreign applications to which priority is claimed by the present application; Dec. 9, 2008.

(Continued)

*Primary Examiner*—Hezron Williams
*Assistant Examiner*—Rodney T Frank
(74) *Attorney, Agent, or Firm*—Workman Nydegger

(57) ABSTRACT

There is described an apparatus for monitoring particles in a fluid stream, comprising a body portion and a detector element that is acoustically decoupled from the body portion. The detector element comprises a target surface, a sample acoustic sensor and a corrosion sensor. The sample acoustic sensor is acoustically coupled to the target surface and is arranged to provide a first signal, which varies in dependence upon acoustic noise generated by impacts of particles and fluid on the target surface. The corrosion sensor is arranged to provide a second signal, which varies in dependence upon corrosion and/or erosion of the target surface. A corresponding method of monitoring particles in a fluid stream is also described. The method and apparatus are suitable for monitoring sand in oil and gas production flow streams.

24 Claims, 4 Drawing Sheets

U.S. PATENT DOCUMENTS

| | | | |
|---|---|---|---|
| 5,681,986 A | 10/1997 | Merk | |
| 6,041,656 A * | 3/2000 | Dunegan | 73/587 |
| 6,360,608 B1 * | 3/2002 | Dunegan | 73/587 |
| 6,693,445 B1 * | 2/2004 | Sutton | 324/700 |
| 6,946,855 B1 * | 9/2005 | Hemblade | 324/700 |
| 7,072,044 B2 * | 7/2006 | Kringlebotn et al. | 356/477 |
| 7,093,482 B2 * | 8/2006 | Berndt | 73/61.75 |

FOREIGN PATENT DOCUMENTS

| | | |
|---|---|---|
| FR | 2 316 594 | 1/1977 |
| GB | 2 408 100 | 5/2005 |
| SU | 1 415 169 | 8/1988 |
| WO | 03/062757 | 7/2003 |

OTHER PUBLICATIONS

Brown G K: "External Acoustic Sensors and Instruments for the Detection of Sand in oil and gas Wells" Annual Offshore Technology Conference, XX, XX, vol. 3, May 8, 1997, pp. 403-420, XP008073401.

* cited by examiner

MONITORING PARTICLES IN A FLUID STREAM

FIELD OF THE INVENTION

The present invention relates to an apparatus for monitoring particles in a fluid stream, and to a method of monitoring particles in a fluid stream. In particular, the present invention relates to monitoring sand in oil and gas production flow streams.

BACKGROUND OF THE INVENTION

It is desirable to be able to monitor particles in a fluid flowing through a conduit. It is particularly desirable to be able to monitor formation sand that is entrained in oil and gas production flow streams. In such systems, the particles may influence erosion, erosion/corrosion and/or corrosion of the conduit surface, potentially leading to breaches of the conduit by the fluid. Therefore, it is important to be able to measure the metal loss of the conduit surface, especially at conduit bends where the metal loss rate is greatest. Nonetheless, it is also important to monitor metal loss on straight sections of a conduit. (It should be noted that, in the art, "corrosion" is a broad term encompassing all types of surface metal loss, including erosion and erosion/corrosion.)

Conventionally, the corrosion of such a conduit surface is measured, for example, by an electrical resistance probe. Such a probe has a sample element that is exposed to the fluid flow such that particles entrained in the fluid flow may impact the sample element. When a particle impacts the sample element in this way, it may corrode the sample element and therefore change the thickness and hence the electrical resistance of the sample element. An electrical resistance probe therefore measures changes in the electrical resistance of its sample element in order to determine the corrosion rate.

A prior art electrical resistance probe is described, for example, in U.S. Pat. No. 6,693,445 (Sutton). In this patent, a probe is disclosed which is suitable for use with an apparatus for monitoring the corrosion of a material by accurately measuring changes in the resistance of an exposed sample element in relation to a protected reference element. The two elements are electrically connected in series via a bridge. The elements are formed from the same piece of material divided by an elongate slot and are proximate to one another so that the temperature difference between them is minimal. This prevents false indications of corrosion by ensuring that the temperature coefficient of the resistivities is the same in both elements. The reference element is covered with a corrosion-resistant layer. This layer is preferably as thin as possible and also a good thermal conductor to further ensure equal temperature of the reference and exposed elements.

Another prior art electrical resistance detector is described in U.S. Pat. No. 6,946,855 (Hemblade), in which an apparatus is disclosed for monitoring the effect on a material of exposure to a fluid, and thereby monitoring the effect on a section of pipe for carrying the fluid. The apparatus includes a sensor element exposed to the fluid and formed as a ring of the material coaxially mounted within, but electrically insulated from, the section of pipe. Changes in the electrical resistance of the sensor element are monitored. Preferably, the apparatus also includes a reference element electrically insulated from the pipe, electrically connected in series to the sensor element and protected from exposure to the fluid. The elements may both be made from the same material as the pipe and, as they are contained within it, experience the same temperature and pressure variations as the pipe. In this manner a change in the resistance of the sensor element caused by corrosion/erosion by the fluid accurately indicates the degree of corrosion/erosion of the pipe carrying the fluid.

In addition to corrosion, excessive numbers of particles entrained in a fluid may cause blockage of the fluid flow through the conduit. Therefore, it is also important to measure the amount of particulate matter entrained in a given fluid stream and correlate this quantity to corrosion.

In the past, the amount of particulate matter has often been estimated based on the measured corrosion rate. However, some particle impacts may not cause corrosion due to insufficient energy and/or a combination of mechanical properties of both particle and surface, potentially transferring all impulse momentum into the elastic region of the material, hence resulting in no permanent deformation or damage of the impacted surface. Or conversely, particulate matter of low mass but high hardness and sharp edges can cause high corrosion rates. Methods to overcome this have been to use softer element materials but such materials are not representative of the pipe, and therefore cannot be used to measure the extent of actual pipe corrosion. A range of particle size, shape and mechanical properties will potentially give different corrosion rates. In addition the particle velocity will affect the corrosion rate, which is another reason that the particle mass is not easy to determine from the corrosion rate alone. Furthermore, the particle velocity is generally determined from another source, and is not representative of the particle velocity at the sensor itself, which introduces further errors. All these factors undermine the possibility of corrosion measurements alone to determine particle mass flowing through a system.

For this reason, the amount of particulate matter entrained in a fluid stream has previously been calculated using a separate acoustic sensor which measures the acoustic noise on the external surface of the conduit. Such an acoustic sensor is often used in addition to an electrical resistance type probe described above. According to the acoustic sensor technique, as a given particle impacts a surface it will give up some of its kinetic energy in the form of impact energy and will produce a surface acoustic emission. An acoustic sensor is therefore positioned to detect these emissions on the external surface of a pipe. The acoustic emission amplitude and frequency response will depend on a number of variables such as where the sensor is situated (e.g. a bend), the flow regime, gas/oil ratios, trajectory of the entrained particles, number of rebounds, and the extent of internal surface area subjected to impact. However, the acoustic noise measured by such a detector will also be contaminated by flow noise and noises from outside the conduit. Methods are employed to separate flow noise and particle impact noise by the means of measuring the frequency response distribution using selective analogue and digital filtering, but these methods are not perfect. In particular, there can be a close overlap of the acoustic signatures of liquids and solids in some situations. Furthermore, very small particles (i.e. "fines" having a dimension less than 25 microns) will go undetected by such a probe because they tend not to create acoustic signals of sufficient amplitude to be detected. In an attempt to overcome some of these problems, the external acoustic sensor is calibrated in situ by injecting sand to characterise the location. However this is costly and impractical, especially in sub-sea locations and potentially introduces unwanted damage during the calibration process. In order to quantify the amount of sand, the particle velocity is again required, since the acoustic energy will depend on both the mass of the particle and the velocity of the particle at the impacted surface. As described above, the particle velocity is generally determined from another source, and is not representative of the particle velocity at the sensor itself, which introduces further errors.

The present invention aims to address these and other such problems with the art by providing a more accurate and versatile apparatus for monitoring particles in a fluid stream flowing through a conduit.

SUMMARY OF THE INVENTION

According to a first aspect of the present invention, there is provided an apparatus for monitoring particles in a fluid stream, comprising a body portion and a detector element that is acoustically decoupled from the body portion. The detector element comprises a target surface; a sample acoustic sensor that is acoustically coupled to the target surface, the sample acoustic sensor being arranged to provide a first signal which varies in dependence upon acoustic noise generated by impacts of particles and fluid on the target surface; and a corrosion sensor arranged to provide a second signal which varies in dependence upon corrosion and/or erosion of the target surface.

Such an apparatus is able to monitor the quantity of particulate matter in a fluid stream as well as the corrosive effects of that particulate matter, such as the erosion rate and the amount of erosion. Furthermore, because the apparatus monitors corrosion and acoustic noise on the same target surface, this enables more accurate differentiation between liquid and solid impact events since the events may be analysed in terms of both their acoustic and corrosive signatures.

Preferably, the detector element is pressure-balanced. More preferably, fluid may flow around substantially the whole detector element thereby pressure balancing the detector element.

In a preferred embodiment, the second signal varies in dependence upon an electrical resistance of the detector element, the electrical resistance of the detector element being related to the corrosion and/or erosion of the target surface. Preferably, the detector element comprises a sample portion that is corrodible and/or erodible by particles impacting on the target surface, the second signal varying in dependence upon an electrical resistance of the sample portion. More preferably, the detector element further comprises a reference portion that is not corrodible and/or erodible by particles impacting on the target surface, and the second signal varies in dependence upon a ratio of the electrical resistance of the sample portion to an electrical resistance of the reference portion.

In another preferred embodiment, the apparatus further comprises temperature measurement means arranged to provide a signal which varies in dependence upon. More preferably again, the temperature measurement means is arranged to provide a signal which varies in dependence upon a temperature of the reference portion.

In yet another preferred embodiment, the detector element further comprises a reference acoustic sensor that is acoustically decoupled from the body portion and the target surface, the reference acoustic sensor being arranged to provide a signal which varies in dependence upon acoustic noise detected by the reference acoustic sensor.

In a further preferred embodiment, the apparatus further comprises pressure measurement means arranged to provide a signal which varies in dependence upon a pressure of the fluid stream.

In a still further preferred embodiment, the apparatus further comprises flow force measurement means arranged to provide a signal which varies in dependence upon a flow force of the fluid stream on the target surface.

Preferably, the pressure measurement means and the flow force measurement means together comprise a differential pressure transducer. More preferably, at least one of the pressure measurement means and the flow force measurement means comprises a piezoelectric element.

Preferably, the target surface comprises a plurality of target surface sections, the corrosion sensor being arranged to provide a plurality of corrosive signals, each corrosive signal varying in dependence upon corrosion and/or erosion of a respective target surface section.

In a preferred embodiment, the target surface is substantially planar. More preferably, the target surface is mounted at an angle to a predominant flow direction.

In an alternative embodiment, the target surface lies within a surface of a cylinder.

There is also provided a choke valve condition monitor for monitoring the condition of a choke valve in a pipe. The monitor comprises a first apparatus (as described above) mounted downstream of the choke valve such that the first and second signals of the first apparatus are condition signals which vary in dependence upon a flow regime at an outlet from the choke valve. The target surface of the first apparatus lies at an internal surface of the pipe. The monitor further comprises a second apparatus (as described above) mounted downstream of the first apparatus such that the first and second signals of the second apparatus are reference signals relating to acoustic and corrosive and/or erosive signatures of particles in the fluid stream. The monitor additionally comprises an output arranged to provide an output signal which varies in dependence upon the condition signals and the reference signals in order to provide an indication of choke valve condition.

There is also provided a method of monitoring the condition of a choke valve in a pipe. The method comprises providing a first apparatus (as described above) mounted downstream of the choke valve such that the first and second signals of the first apparatus are condition signals which vary in dependence upon a flow regime at an outlet from the choke valve. The target surface of the first apparatus lies at an internal surface of the pipe. The method further comprises providing a second apparatus (as described above) mounted downstream of the first apparatus such that the first and second signals of the second apparatus are reference signals relating to acoustic and corrosive and/or erosive signatures of particles in the fluid stream. The method additionally comprises comparing the condition signals and the reference signals in order to provide an indication of choke valve condition.

According to a second aspect of the present invention, there is provided a method of monitoring particles in a fluid stream, comprising: providing an apparatus having a body portion and a detector element, the detector element being acoustically decoupled from the body portion, and the detector element having a target surface; measuring acoustic noise generated by impacts of particles and fluid on the target surface; and measuring corrosion and/or erosion of the target surface.

In a preferred embodiment, the method further comprises measuring a flow force of the fluid stream on the target surface. In another preferred embodiment, the method further comprises measuring a pressure of the fluid stream. In yet another preferred embodiment, the method further comprises measuring a temperature of the fluid stream.

Preferably, the method further comprises correlating the measured acoustic noise and the measured corrosion and/or erosion. More preferably, the measured pressure, temperature, and/or flow force may also be correlated with the measured acoustic noise and the measured corrosion and/or erosion.

According to a third aspect of the present invention, there is provided an apparatus for monitoring particles in a fluid stream, comprising a body portion and a detector element that is acoustically decoupled from the body portion. The detector element comprises a target surface; a sample acoustic sensor that is acoustically coupled to the target surface, the sample acoustic sensor being arranged to provide a first signal which varies in dependence upon acoustic noise generated by impacts of particles and fluid on the target surface; and a reference acoustic sensor that is acoustically decoupled from the body portion and the target surface, the reference acoustic sensor being arranged to provide a second signal which varies in dependence upon acoustic noise detected by the reference acoustic sensor.

Such an apparatus enables the first (sample) signal to be compensated for small temperature and pressure variations which are also present in the second (reference) signal.

According to a fourth aspect of the present invention, there is provided a method of monitoring particles in a fluid stream, comprising: providing an apparatus having a body portion and a detector element, the detector element being acoustically decoupled from the body portion, and the detector element having a target surface; measuring acoustic noise generated by impacts of particles and fluid on the target surface; providing a reference acoustic sensor that is acoustically decoupled from the body portion and the target surface; and measuring acoustic noise detected by the reference acoustic sensor.

According to a fifth aspect of the present invention, there is provided an apparatus for monitoring particles in a fluid stream, comprising a body portion and a detector element that is acoustically decoupled from the body portion. The detector element comprises a target surface; a sample acoustic sensor that is acoustically coupled to the target surface, the sample acoustic sensor being arranged to provide a first signal which varies in dependence upon acoustic noise generated by impacts of particles and fluid on the target surface; and flow force measurement means arranged to provide a second signal which varies in dependence upon a flow force of the fluid stream on the target surface.

Such an apparatus enables the flow force and the acoustic noise to be monitored on the same target surface, thereby allowing these quantities to be correlated to provide more accurate measurements than in the prior art.

According to a sixth aspect of the present invention, there is provided a method of monitoring particles in a fluid stream, comprising: providing an apparatus having a body portion and a detector element, the detector element being acoustically decoupled from the body portion, and the detector element having a target surface; measuring acoustic noise generated by impacts of particles and fluid on the target surface; and measuring a flow force of the fluid stream on the target surface.

According to a seventh aspect of the present invention, there is provided an apparatus for monitoring particles in a fluid stream, comprising a body portion; and a detector element. The detector element comprises a target surface; a corrosion sensor arranged to provide a first signal which varies in dependence upon corrosion and/or erosion of the target surface; and flow force measurement means arranged to provide a second signal which varies in dependence upon a flow force of the fluid stream on the target surface.

Such an apparatus enables the flow force and the corrosion to be monitored on the same target surface, thereby allowing these quantities to be correlated to provide more accurate measurements than in the prior art.

According to an eighth aspect of the present invention, there is provided a method of monitoring particles in a fluid stream, comprising: providing an apparatus having a body portion and a detector element, the detector element being acoustically decoupled from the body portion, and the detector element having a target surface; measuring acoustic noise generated by impacts of particles and fluid on the target surface; and measuring a flow force of the fluid stream on the target surface.

Other preferred features of the present invention are set out in the appended claims.

BRIEF DESCRIPTION OF THE DRAWINGS

Embodiments of the present invention will now be described by way of example with reference to the accompanying drawings in which.

DETAILED DESCRIPTION OF A PREFERRED EMBODIMENT

Figure 1:
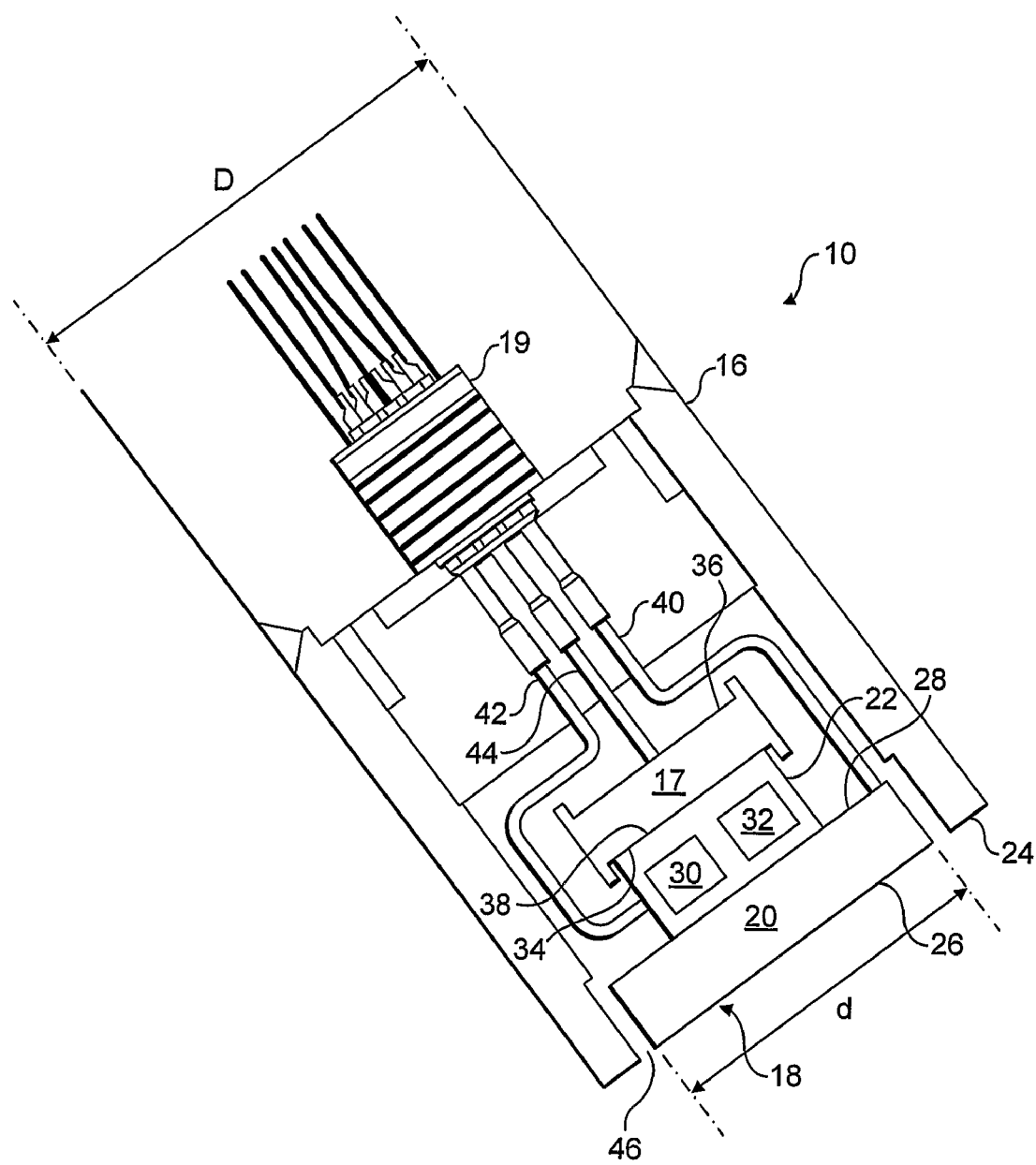
FIG. 1 is a section through an apparatus according to one embodiment of the present invention.
Figure 2:
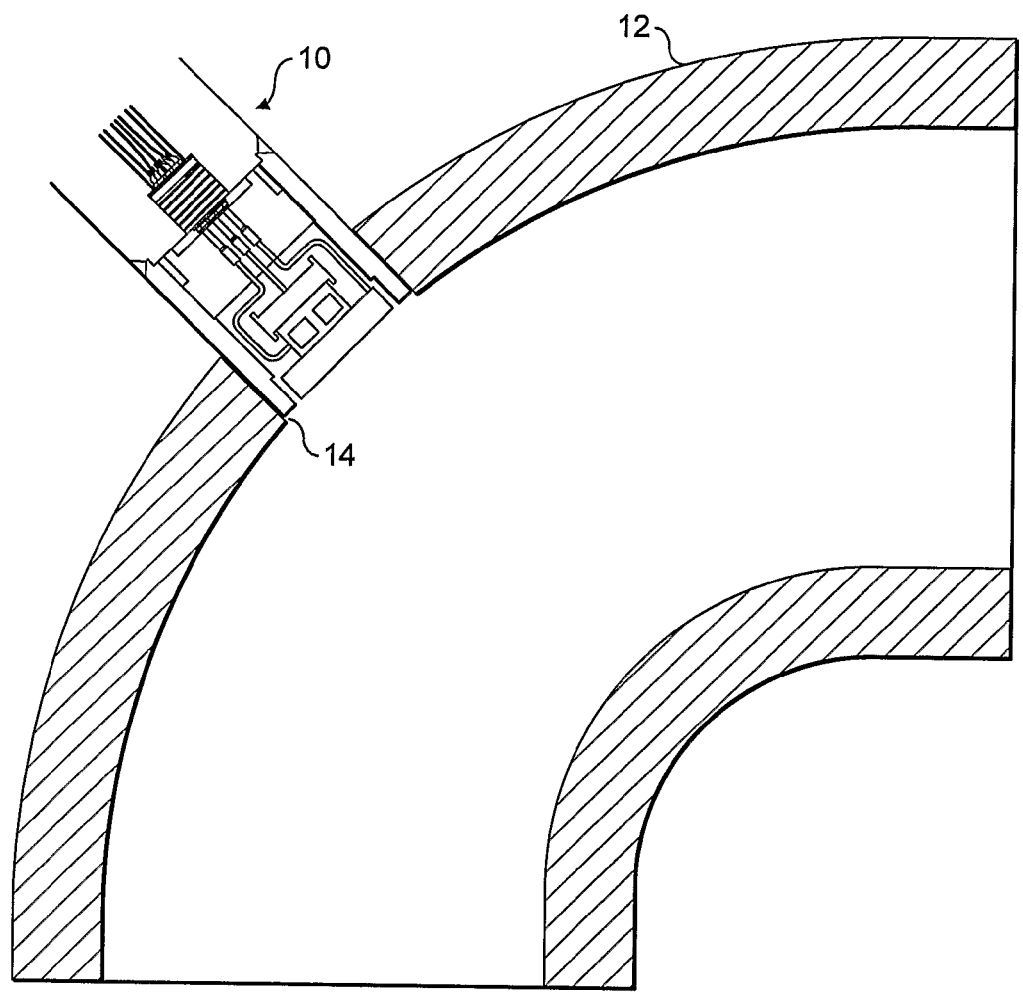
FIG. 2 shows the apparatus of FIG. 1 mounted on a bend of a pipe.

FIG. 1 shows a section through an apparatus according to one embodiment of the present invention. In FIG. 1 the apparatus is a probe 10 for monitoring particles in a fluid stream flowing through a conduit. The probe 10 is intended to be flush mounted on an external bend of a pipe 12, as shown in FIG. 2. Thus there is an opening 14 in the pipe 12 through which the probe 10 is inserted.

Referring to FIG. 1, the probe 10 comprises a probe housing 16 within which there is a differential pressure transducer 17 and a detector element 18. An electrical connector 19 located at the back of the probe 10 provides an output from the probe 10. The detector element 18 comprises a target portion 20 and an acoustic sensing portion 22. In a preferred embodiment, the detector element 18 is made of the same material as the inside surface of the pipe 12 so that it will corrode in the same way as the pipe 12. The target portion 20, the acoustic sensing portion 22, and the transducer 17 are each individually electrically connected to the electrical connector 19 at the rear of the probe 10. The electrical connector 19 provides the pressure containment of the probe 10 and is a feedthrough assembly rated for temperature and pressure and chemical compatibility.

The target portion 20 is located at a front end 24 of the probe 10. Viewed from the front end 24, the probe 10 is circular in cross-section having a diameter D. The target portion has a target surface 26 and a back surface 28. The target surface 26 is substantially coplanar with the front end 24 of the probe 10, and is circular having a diameter d. Thus a front surface area of the target portion 20 is known. In a preferred embodiment, D is approximately 50 mm and d is approximately 35-40 mm.

The target portion 20 comprises a sample portion (not shown) that is exposed to corrosive effects of a fluid flow across the target surface 26 of the target portion 20. The target portion 20 further comprises a reference portion (not shown) that is protected from the corrosive effects of a fluid flow across the target surface 26 of the target portion 20. The target portion 20 has a corrosion sensor (not shown) that is arranged to provide a signal which varies in dependence upon an amount of corrosion of the target portion 20.

In a preferred embodiment, the corrosion sensor is an electrical resistance sensor. Thus, the sensor is arranged to detect changes in an electrical resistance of the sample portion which result from loss of material of the sample portion due to corrosion. Errors due to temperature and pressure inhomogeneities may be compensated for by additionally detecting changes in an electrical resistance of the reference portion (as the sample portion and the reference portion are subject to the same temperature and pressure effects). Thus, for the purposes of temperature and pressure compensation, the sensor is arranged to provide a compensated electrical resistance signal which varies in dependence upon a ratio of the electrical resistance of the sample portion to the electrical resistance of the reference portion. In a preferred embodiment, the sensor is further arranged to provide a signal which varies in dependence upon a temperature of the reference portion, which is the same as the process temperature T. In particular, the temperature T may be determined from the electrical resistance of the reference portion.

Such an electrical resistance sensor is described in U.S. Pat. No. 6,693,445 (Sutton), in which the sample portion and the reference portion are electrically connected in series via a bridge and are connected to a current generator which drives current through the series circuit. The electronic circuitry further comprises voltage monitoring means arranged to monitor the voltage developed across each of the sample portion and reference portion. The sample portion and reference portion of the sensor are situated proximate to each other to help ensure that the temperature difference between the sample portion and the reference portion is minimal and the reference portion has good thermal contact with the environment, such as the fluid in the pipe 12. The reference portion may be protected from corrosion by means of a thin protective covering, such as a non-corrosive metallic cover layer made of gold, platinum, chromium, or any other relatively inert metal or other metal which does not corrode to any significant degree when exposed to the fluid in question. The electrical resistance sensor may be configured to monitor process temperature T. A calibration resistor may be included in the electronic circuitry in series with the sample portion and the reference portion. Such a calibration resistor provides for monitoring the temperature of the target portion 20, and hence the process temperature T of the fluid, without the need for a special temperature sensor.

In an alternative embodiment, the corrosion sensor need not be an electrical resistance sensor. Instead, an alternative metal loss sensor could be used, such as a radioactivity sensor.

The detector element 18 is acoustically decoupled from the pipe 12 and the probe housing 16. In the embodiment of FIGS. 1 and 2, the acoustic decoupling is accomplished by means of a "pressure-balanced floating arrangement". In this arrangement, the detector element 18 and the transducer 17 are supported within a sensor housing (not shown). The sensor housing is constrained within the probe housing 16 by means of an acoustic decoupling compound (not shown) between the internal wall of the probe housing 16 and an external surface of the sensor housing. Further acoustic decoupling is provided by means of a gap 46 between the detector element 18 and the probe housing 16. A first connector 40 extends between the electrical connector 19 and the target portion 20. A second connector 42 extends between the electrical connector 19 and the acoustic sensing portion 22. A third connector 44 extends between the electrical connector 19 and the transducer 17. The connectors 40, 42 and 44 are flexible so as to provide sufficient acoustic decoupling from the feed-through connector 19. The "pressure-balanced floating arrangement" therefore provides enough support to prevent vibrations of the detector element 18 and transducer 17, but does not acoustically couple the detector element 18 and transducer 17 to the probe housing 16.

The acoustic sensing portion 22 is affixed to the back surface 28 of the target portion 20. In a preferred embodiment, the acoustic sensing portion 22 is integrally formed with the target portion 20. The acoustic sensing portion 22 comprises a sample acoustic sensor 30 and a reference acoustic sensor 32. The two acoustic sensors 30 and 32 are thermally and mechanically balanced within the detector element 18. The sample acoustic sensor 30 is acoustically coupled to the detector element 18, whereas the reference acoustic sensor 32 is acoustically decoupled from the detector element 18. In particular, the acoustic sensors 30 and 32 may be mounted within two distinct chambers. The sample acoustic sensor 30 is mounted within oil, whereas a sensitized part of the reference acoustic sensor chamber is nitrogen filled.

The transducer 17 has a front diaphragm 34 and a back diaphragm 36, and is located behind the acoustic sensing portion 22. In a preferred embodiment, the front diaphragm 34 is in contact with a back surface 38 of the acoustic sensing portion 22 of the detector element 18. The back surface 38 of the acoustic sensing portion 22 is in direct contact with and energised against the front diaphragm 34, but is not sealed. The transducer 17 comprises at least one piezoelectric element (not shown).

In use, fluid and entrained particles travel along the pipe 12 and may impact on the target surface 26 of the target portion 20 of the probe 10.

The probe 10 should be located such that there is a high incident rate of particles impacting on the target surface 26. Therefore, as shown in FIG. 2, an apparatus according to a preferred embodiment of the present invention is a flush probe 10 mounted on an external bend of a pipe 12. By flush mounting the probe 10 on an external bend of the pipe 12, the probe 10 is mounted at an angle to a predominant flow direction. The mounting angle is dictated by the pipework geometry and anticipated flow regime. Furthermore, the probe 10 is positioned flush to the pipe wall to give actual wall thickness loss measurement of the pipe 12. However, it will be understood that non-flush probes may also be provided according alternative embodiments of the present invention (not shown). For example, if it is difficult to mount a probe at a bend (e.g. due to space constraints), then an intrusive probe with an angled head may be used instead. Such a probe would protrude within the pipe 12 such that the front face of the detector element would be at an angle of approximately 45° to the predominant flow direction to thereby emulate the conduit surface at the bend (where the corrosion is generally greatest). However, use of a flush probe 10 with a flat target surface 26 is preferred in order to prevent any unnecessary disturbances of the flow regime.

The fluid and entrained particles are at a process pressure p and process temperature T. In an oil and gas production flow stream, p may be as high as about $1 \times 10^8$ Pa (15,000 psi) and T may be as high as about 180° C. Thus, the probe 10 is built to withstand temperatures and pressures of this magnitude.

As discussed above, the process temperature T can be measured by sensing the change in electrical resistance of the reference portion of the target portion 20.

The gap 46 between the detector element 18 and the probe housing 16 allows the fluid flowing within the pipe 12 to enter the space between the probe housing 16 and the combined transducer 17 and detector element 18 arrangement. Nonetheless, the fluid flow rate through this space is negligible compared to the fluid flow rate through the pipe 12, but allows for near instantaneous transfer of heat and pressure. Thus, the back diaphragm 36 of the transducer 17 is subject only to the process pressure p and can therefore be used to measure the process pressure.

Due to the floating arrangement of the detector element 18, the back surface 28 of the target portion 20 is subject to the same process pressure as the target surface 26, and so on, such that the arrangement can be described as "pressure-balanced". The pressure-balanced arrangement enables the probe 10 to withstand high temperatures and pressures.

Furthermore, the pressure-balanced arrangement minimises strain based deflections and thermal gradients of the detector element 18 and thereby reduces potential errors in the acoustic signal and the electrical resistance signal which may otherwise result from strain related distortions of the acoustic sensing portion 22 and the target portion 20.

The target surface 26 of the target portion 20 is subject to the process pressure p and flow force of the system. The front diaphragm 34 of the transducer 17 is coupled to the detector element 18 such that the front diaphragm is subject to the process pressure and flow force of the system. Thus, the differential pressure between the front diaphragm 34 and the back diaphragm 36 may be used to measure the flow force.

Due to the acoustic decoupling of the detector element 18 and the transducer 17 from the housing 16 and the pipe 12, the detector element 18 is not sensitised to detect an unpredictable acoustic noise field related to acoustic signals generated in the vicinity of the associated pipe work and probe housing 16 due to a complex set of fluid flow regimes, particle trajectories and impact responses. Thus, the acoustic noise detected by the acoustic sensing portion 22 is isolated to the detector element 18 of known characteristics, such that the full spectrum of detected acoustic noise is limited to that which has been transferred from the flowing fluid onto the detector element 18.

Since the reference acoustic sensor 32 is located within the acoustic sensing portion 22 of the detector element 18, this sensor 32 is also acoustically decoupled from the housing 16 and the pipe 12. Furthermore, the two acoustic sensors 30 and 32 are identically mounted within the acoustic sensing portion 22 except that the reference acoustic sensor 32 is acoustically decoupled from the detector element 18 (in contrast to the sample acoustic sensor 30 which is acoustically coupled to the detector element 18). Thus, the reference acoustic sensor 32 experiences near identical process temperature and pressure effects which may then be used to compensate for any process induced offset and transient errors of the sample acoustic sensor 30. Hence, a temperature and pressure compensated acoustic signal may be derived based on the acoustic noise sensed by the two acoustic sensors 30 and 32, and this compensated acoustic signal is related only to the acoustic noise produced on the detector element 18 by the fluid flow and entrained particles impinging on the target surface 26 of the target portion 20 of the detector element 18.

The compensated acoustic signal is related to a number of key influencing factors such as the acoustic characteristics of target portion 20 (which are known), and the acoustic characteristics of the flow transferring acoustic energy onto the target surface 26. The detector element 18 of the probe 10 can be characterised and calibrated for a given set of temperatures and pressures with a range of velocities or flow forces, for various fluid (oil/gas/water) ratios and for various solids entrained in the flow (mass, size and density), and so on.

The compensated acoustic signal may be analysed in both the time domain and the frequency domain.

In the time domain, the energy of the compensated acoustic signal is proportional to the mass density events on the target surface 26, and the power is proportional to the rate of change of that energy with respect to time, which is a function of the velocity of the mass densities of the fluid and particles.

In the frequency domain, the spectrum of the compensated acoustic signal depends on the types of gas or liquid or solid acting on the target surface 26. Flowing gas produces a low amplitude, continuous signal within a frequency range associated with gases. Liquids produce a higher amplitude signal than gases (due to their higher density), and the signal is discontinuous and at a higher frequency than a gas signal. Solids produce an even higher amplitude signal (dependant on mass and velocity, etc.), but a solid signal is of shorter duration than a liquid signal, and is at a higher frequency again than the liquid signal.

Having identified a means to partition the compensated acoustic signal in both the time and frequency domains, the analysis of the fluids/solids spectrum is advanced. When a solid impacts the target surface 26, the impact duration time will vary (e.g. dependent on relative hardness of surfaces and impact strength), and the energy converted into acoustic energy will also vary according to the particle mass, velocity and coefficient of restitution of the event. These events can be counted and logged according to amplitude and rise time of the compensated acoustic signal, and particle energy may consequently be determined.

There can be a close overlap of the acoustic characteristics of liquids and solids, so the associated acoustic responses can easily be confused in some situations, resulting in potentially higher estimates of solids content. Furthermore, in high velocity liquid/gas mixtures, fine mists can cause spectra similar to fine solids, or, conversely, larger droplets can cause acoustic signals similar to softer solids.

However, it is known that liquids do not generally cause erosion damage (unless, in the limiting velocity, they cause a breakdown of the corrosion durable oxide layer which leads to erosion/corrosion phenomena), whereas solids can be highly erosive compared to liquids.

According to an embodiment of the present invention, the probe 10 simultaneously measures the corrosive and acoustic effects of the events on the same detector element 18. Thus, the corrosion events (in terms of the compensated electrical resistance signal) may be correlated with the acoustic events (in terms of the compensated acoustic signal) to resolve any ambiguities in the liquid/solid acoustic spectrum. For example, an acoustic event having an uncertain liquid/solid acoustic signature is likely to have been caused by a solid if there is a corresponding corrosive event, but is likely to have been caused by liquid if there is no corresponding corrosive event.

In addition, very small solid particles (i.e. "fines" having a dimension less than 25 microns) tend not to create acoustic signals of sufficient amplitude to be detected. Therefore, these fines would not be detected by an acoustic sensor alone. However, fines can still produce corrosive effects. Therefore, an apparatus according to an embodiment of the present invention can offer a qualitative indication of fine solids due to their corrosive effect in the absence of an acoustic signal.

Hence, an apparatus according to an embodiment of the present invention offers significant advantages over acoustic detectors and/or electrical resistance probes of the prior art.

Having identified the energy/power of the acoustic signals impacting the target surface 26, and having characterised the gas, liquid and solids profiles by acoustic spectra and corrosion measurements, and having counted the impact events according to rise time and amplitude, the mass of a particle is still unknown without knowledge of the velocity of the fluid/particle. Therefore, the next step is to qualitatively detect the changes in the flow force acting on the pressure-balanced detector element in order to derive a mean velocity of the fluid stream.

As described above, the differential pressure between the front diaphragm 34 and the back diaphragm 36 of the transducer 17 may be used to measure the flow force on the target surface 26. The flow force R may be written as:

$$R = \rho A v^2 \sin\theta \quad (1)$$

where $\rho$ is the effective mass density, A is the area of the target surface 26 (i.e. $A = \pi(d/2)^2$), v is the fluid velocity, and $\theta$ is the angle of incidence of the flow to the target surface 26 of the detector element 18. The effective mass density $\rho$ is influenced by the compressible fluid density, a function of fluid pressure and temperature, and the volumetric ratio of entrained liquids (oil, condensate, droplets) and solids (particulates). Then:

$$R = A v^2 \sin\theta (a\rho_{gas} + b\rho_{liquids} + c\rho_{solids}) \quad (2)$$

where a, b and c are the effective partial volumes of gas, liquids and solids in the fluid stream, liquids and solids are deemed as incompressible, and $\rho_{gas}$ is a function of the measured process pressure p and temperature T, and $pV = nR_oT$.

The measured flow force R is then converted into mean fluid velocity v. The mean fluid velocity v may be used with the particle energy equation ($E = (½)mv^2$) to derive the cumulative mass rate of the particles with corrections for liquid signals using the corrosion detection signal (i.e. the compensated electrical resistance signal).

The known surface area of the target surface 26 of the detector element 18 can then be used to extrapolate the particle density across the cross section of the pipe 12. The derivation of the quantity of particles flowing through the pipe section can be calculated, if it can be assumed the particle density flowing through the pipe 12 is constant. Clearly this assumption cannot be made without an analysis of the flow regime around the probe 10 and the associated pipe work. However this can be overcome by computational fluid modelling to determine the particle trajectory in the vicinity of the probe 10 and a representative model con provide an indication of the particle distribution density.

Having identified the flow characteristics in terms of temperature and pressure, with a qualitative indication of changes of flow velocity we are able to characterise the flow in terms of gas, non-erosive liquids and solids content. By correlating acoustic energy signals in the solids spectrum with flow velocity and assuming constant mass density it is possible to derive particle numbers in a range of particle sizes. In this way, the particle size spectrum is correlated with the corresponding particle erosiveness for a given velocity profile under the pressure and temperature conditions. Hence, we not only derive the particle mass, size and solids production rate profile of the reservoir under the changing operating conditions and the corresponding erosive damage in that actual location, but we also gain a profile of the potential cumulative amount of erosion damage elsewhere in the system exposed to similar trajectories.

Thus, an apparatus according to an embodiment of the present invention may be used to determine both the amount of particulate matter in a fluid stream and the corrosive effect of that particulate matter.

Figure 3:
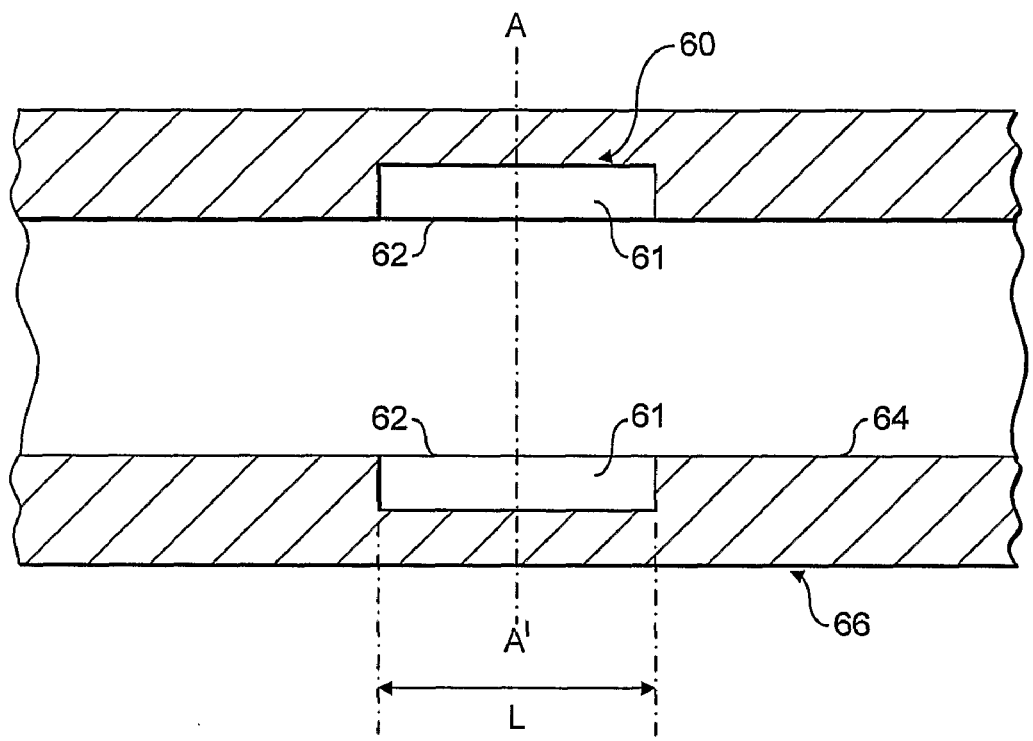
FIG. 3 is a schematic representation of an apparatus according to a second embodiment of the present invention mounted on a straight section of a pipe.
Figure 4:
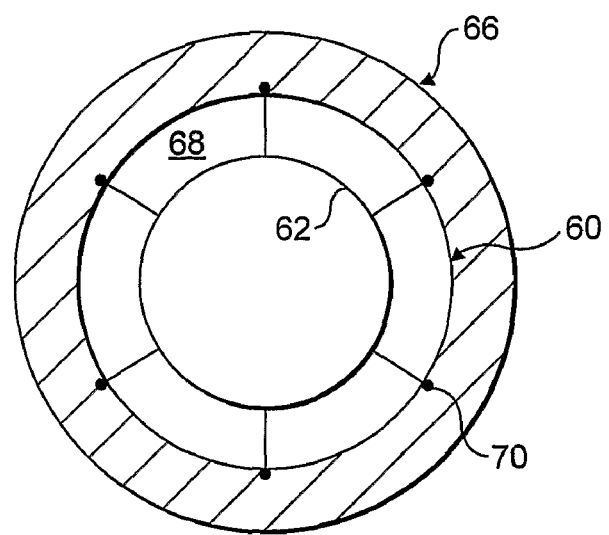
FIG. 4 is a section through the apparatus of FIG. 3 along line AA'.

An apparatus according to a second embodiment of the present invention is shown schematically in FIGS. 3 and 4. In this embodiment, the apparatus 60 is substantially formed as an open cylinder/ring and is intended to monitor particle impacts, and corrosion and/or erosion events, along a straight section of pipe.

The apparatus 60 comprises a body portion (not shown) and a detector element 61 having a target surface 62. The target surface 62 is substantially flush with an internal surface 64 of a straight section of a pipe 66. Thus, the target surface 62 is formed as an internal surface of a cylinder/ring.

The detector element 61 is acoustically decoupled from the body portion and from the pipe 66 by means of an appropriately selected acoustic decoupling material. The detector element 61 comprises an acoustic sensor (not shown) that is acoustically coupled to the target surface 62. The acoustic sensor is arranged to provide an acoustic signal which varies in dependence upon acoustic noise generated by impacts of particles and fluid on the cylindrical target surface 61. The detector element 61 further comprises a corrosion sensor arranged to provide a corrosion signal which varies in dependence upon corrosion and/or erosion of the target surface. Preferably, the corrosion sensor is an electrical resistance sensor.

It is also possible to incorporate a reference acoustic sensor and a reference corrosion sensor into the apparatus 60 to compensate for temperature and pressure inhomogeneities (see the description above relating to the reference portion and sample portion of the embodiment of FIGS. 1 and 2).

FIG. 4 shows a section through the arrangement of FIG. 3 along line AA'. In a preferred embodiment, the detector element 61 and the target surface 62 comprise a plurality of sectors 68 for the purpose of monitoring corrosion and/or erosion. FIG. 4 depicts six sectors 68 that each extend along the full longitudinal length L of the cylindrical target surface 62. The sectors 68 each extend along a respective circumferential portion of the target surface 62. In FIG. 4, the sectors 68 each extend along a respective 60 degree portion of the cylindrical target surface 62. The boundaries between the sectors 68 define pick-off points 70 where the detector portion is connected to the electronic circuitry to measure electrical resistance. In this way, it is possible to monitor the electrical resistance in each sector 68, and hence the corrosion and/or erosion in each sector 68. Thus, if there is a different amount of erosion in each sector, this may be indicative of an anomalous flow regime in that section of pipe, e.g. due to a partial blockage upstream.

A corrosion sensor having sectors as described above is disclosed in U.S. Pat. No. 6,946,855 (Hemblade).

The sectors 68 are acoustically coupled, so only one acoustic sensor is required, but this single acoustic sensor cannot differentiate between particle impacts occurring in different sectors 68.

Figure 5:
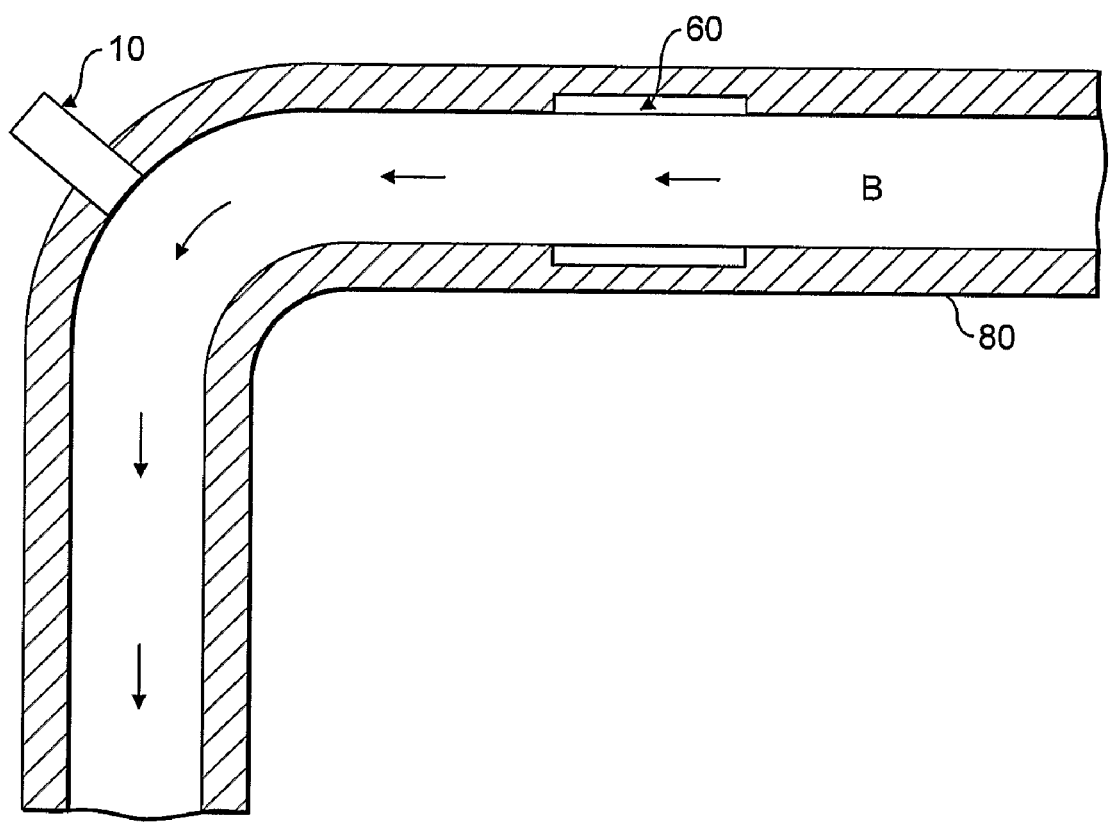
FIG. 5 shows an arrangement including the apparatus of FIG. 1 and the apparatus of FIG. 3 within a single section of pipe.

FIG. 5 shows an arrangement including both the flush probe 10 of FIG. 1 and the cylindrical apparatus 60 of FIG. 3 to monitor particles in a fluid stream within a single section of pipe 80.

Let us assume that both detectors are simultaneously being used to monitor particles in the fluid stream, and that the acoustic and corrosion measurements from each of these detectors remain approximately constant and the ratio of these measurements remains approximately constant. If the measurements from the flush probe 10 continue to remain constant while the measurements from the cylindrical apparatus 60 start to vary, this is likely to be indicative of a change of flow regime, rather than a change in the quantity/qualities of the particulate matter in the fluid stream.

One application of this arrangement would be as a choke valve condition monitor. Choke valves are used to choke back the flow in oil and gas production flow streams. Choke valves in wellheads tend to fail due to erosion, corrosion, cavitation and vibration caused by sand particles. The choke valve stem (i.e. the shaft that is adjusted up and down to change the extent of choking back the flow) can get damaged by the sand at high flow rates. When the stem gets damage, the flow jets become unstable and create "preferential flow" (i.e. a highly concentrated high velocity jet with entrained particles) at the outlet from the valve. This preferential flow results in very high localised erosion and corrosion/erosion rates at the outlet of the valve which indicate that the choke valve is failing.

Let us assume that there is a choke valve positioned near point B in FIG. 5, slightly upstream of the cylindrical apparatus 60, which is itself slightly upstream of a bend in the pipe 80 where the flush probe 10 is mounted.

Prior to generating a large (and damaging) erosive signal, the preferential flow would generate an amplified acoustic signal at the cylindrical apparatus 60 due to the much higher velocity, increased angle of impingement and increased number of particles hitting the target surface 62.

Of course, an amplified acoustic signal on the target surface 62 could be due to more sand or to preferential flow. Therefore, the probe 10 downstream of the apparatus 60 is used to determine the present corrosion and acoustic signatures of the flow, which can then be correlated with the corrosion and acoustic signals from the apparatus 60.

Thus, such an arrangement can be used as a choke valve condition monitor. In addition, such an arrangement would inform the operator of the historical performance of the choke (i.e. this amount of sand at this velocity with this erosion characteristic created this life expectancy of the choke).

Although preferred embodiments of the invention have been described, it is to be understood that these are by way of example only and that various modifications may be contemplated.

The invention claimed is:

1. An apparatus for monitoring particles in a fluid stream, comprising:
   a body portion; and
   a detector element that is acoustically decoupled from the body portion, the detector element comprising:
   a target surface;
   a sample acoustic sensor that is acoustically coupled to the target surface, the sample acoustic sensor being arranged to provide a first signal which varies in dependence upon acoustic noise generated by impacts of particles and fluid on the target surface; and
   a corrosion sensor arranged to provide a second signal which varies in dependence upon corrosion and/or erosion of the target surface.

2. The apparatus of claim 1 in which the detector element is pressure-balanced.

3. The apparatus of claim 2 in which fluid may flow around substantially the whole detector element thereby pressure balancing the detector element.

4. The apparatus of claim 1 in which the second signal varies in dependence upon an electrical resistance of the detector element, the electrical resistance of the detector element being related to the corrosion and/or erosion of the target surface.

5. The apparatus of claim 4 in which the detector element comprises a sample portion that is corrodible and/or erodible by particles impacting on the target surface, the second signal varying in dependence upon an electrical resistance of the sample portion.

6. The apparatus of claim 5 in which the detector element further comprises a reference portion that is not corrodible and/or erodible by particles impacting on the target surface, and the second signal varies in dependence upon a ratio of the electrical resistance of the sample portion to an electrical resistance of the reference portion.

7. The apparatus of claim 1 further comprising temperature measurement means arranged to provide a signal which varies in dependence upon the temperature of the fluid stream.

8. The apparatus of claim 6 further comprising temperature measurement means arranged to provide a signal which varies in dependence upon the temperature of the fluid stream, in which the temperature measurement means is arranged to provide a signal which varies in dependence upon a temperature of the reference portion.

9. The apparatus of claim 1 in which the detector element further comprises a reference acoustic sensor that is acoustically decoupled from the body portion and the target surface, the reference acoustic sensor being arranged to provide a signal which varies in dependence upon acoustic noise detected by the reference acoustic sensor.

10. The apparatus of claim 1 further comprising pressure measurement means arranged to provide a signal which varies in dependence upon a pressure of the fluid stream.

11. The apparatus of claim 1 further comprising flow force measurement means arranged to provide a signal which varies in dependence upon a flow force of the fluid stream on the target surface.

12. The apparatus of claim 1 further comprising pressure measurement means arranged to provide a signal which varies in dependence upon a pressure of the fluid stream, further comprising flow force measurement means arranged to provide a signal which varies in dependence upon a flow force of the fluid stream on the target surface, in which the pressure measurement means and the flow force measurement means together comprise a differential pressure transducer.

13. The apparatus of claim 12 in which at least one of the pressure measurement means and the flow force measurement means comprises a piezoelectric element.

14. The apparatus of claim 1 in which the target surface comprises a plurality of target surface sections, the corrosion sensor being arranged to provide a plurality of corrosive signals, each corrosive signal varying in dependence upon corrosion and/or erosion of a respective target surface section.

15. The apparatus of claim 1 in which the target surface is substantially planar.

16. The apparatus of claim 15 in which the target surface is mounted at an angle to a predominant flow direction.

17. The apparatus of claim 1 in which the target surface lies within a surface of a cylinder.

18. A choke valve condition monitor for monitoring the condition of a choke valve in a pipe, comprising:
   a first apparatus according to claim 1 mounted downstream of the choke valve such that the first and second signals of the first apparatus are condition signals which vary in dependence upon a flow regime at an outlet from the choke valve, the target surface of the first apparatus forming an internal cylindrical surface of the pipe;

a second apparatus according to claim 1 mounted downstream of the first apparatus such that the first and second signals of the second apparatus are reference signals relating to acoustic and corrosive and/or erosive signatures of particles in the fluid stream, the target surface of the second apparatus being substantially planar; and an output arranged to provide an output signal which varies in dependence upon the condition signals and the reference signals in order to provide an indication of choke valve condition.

19. A method of monitoring the condition of a choke valve in a pipe, comprising:

providing a first apparatus according to claim 1 mounted downstream of the choke valve such that the first and second signals of the first apparatus are condition signals which vary in dependence upon a flow regime at an outlet from the choke valve, the target surface of the first apparatus forming an internal cylindrical surface of the pipe;

providing a second apparatus according to claim 1 mounted downstream of the first apparatus such that the first and second signals of the second apparatus are reference signals relating to acoustic and corrosive and/or erosive signatures of particles in the fluid stream, the target surface of the second apparatus being substantially planar; and comparing the condition signals and the reference signals in order to provide an indication of choke valve condition.

20. A method of monitoring particles in a fluid stream, comprising:

providing an apparatus having a body portion and a detector element, the detector element being acoustically decoupled from the body portion, and the detector element having a target surface;

measuring acoustic noise generated by impacts of particles and fluid on the target surface; and measuring corrosion and/or erosion of the target surface.

21. The method of claim 20 further comprising measuring a flow force of the fluid stream on the target surface.

22. The method of claim 20 further comprising measuring a pressure of the fluid stream.

23. The method of claim 20 further comprising measuring a temperature of the fluid stream.

24. The method of claim 20 further comprising correlating the measured acoustic noise and the measured corrosion and/or erosion.

\* \* \* \* \*

UNITED STATES PATENT AND TRADEMARK OFFICE
CERTIFICATE OF CORRECTION

Page 1 of 1

PATENT NO.       : 7,878,047 B2
APPLICATION NO.  : 12/092252
DATED            : February 1, 2011
INVENTOR(S)      : Hemblade It is certified that error appears in the above-identified patent and that said Letters Patent is hereby corrected as shown below:

Column 7
Line 33, change "current" to --a current--

Column 8
Line 50, change "according" to --according to--

Signed and Sealed this
Ninth Day of August, 2011

David J. Kappos
*Director of the United States Patent and Trademark Office*